United States Patent [19]

Fifolt et al.

[11] 4,343,951
[45] Aug. 10, 1982

[54] METHOD FOR THE PREPARATION OF FLUOROANILINE

[75] Inventors: Michael J. Fifolt, Grand Island, N.Y.; Arthur M. Foster, Birmingham, Mich.

[73] Assignee: Hooker Chemicals & Plastics Corp., Niagara Falls, N.Y.

[21] Appl. No.: 220,671

[22] Filed: Dec. 29, 1980

[51] Int. Cl.³ .................... C07C 85/00; C07C 85/12; C07C 85/24
[52] U.S. Cl. ...................................... 564/414; 564/442
[58] Field of Search ............................... 564/442, 414

[56] References Cited

U.S. PATENT DOCUMENTS 4,145,364 3/1979 Mulvey et al. ............... 564/442 X
4,198,348 4/1980 Bertini et al. ...................... 564/414

OTHER PUBLICATIONS

Petrov et al., "Dokl. Akad. Nauk SSSR", vol. 179(2), pp. 356 and 357, (1968).
Bentley et al., "Chem. Ab.", vol. 78, Ab. No. 124216e, (1973).

*Primary Examiner*—John Doll
*Attorney, Agent, or Firm*—James F. Tao; Arthur S. Cookfair

[57] ABSTRACT

A process for the preparation of fluoroaniline compounds comprises the steps of
(A) reacting an ammonium fluorophthalamate or a fluorophthalamic acid of the formula

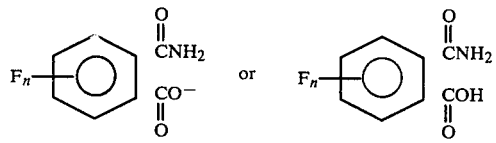

where n is 1 or 2 with an alkali or an alkali earth metal hypochlorite to form the corresponding fluoroanthranilic acid; and
(B) decarboxylating the fluoroanthranilic acid by reaction with a mineral acid to form the corresponding fluoroaniline of the formula

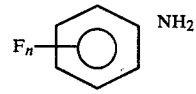

where n is as previously defined.

19 Claims, No Drawings

METHOD FOR THE PREPARATION OF FLUOROANILINE

BACKGROUND OF THE INVENTION

This invention relates to a process for the preparation of fluorinated aromatic compounds and in particular to a process for the preparation of fluoro-anthranilic acids and fluoroanilines. The fluoroanilines and fluoroanthranilic acids are valuable as chemical intermediates for the further preparation of various dyestuffs, pesticides, and pharmaceuticals.

SUMMARY OF THE INVENTION

In accordance with this invention there is provided a process for the preparation of fluoroaniline compounds comprising (A) reacting ammonium fluorophthalamate or a fluorophthalamic acid of the formula

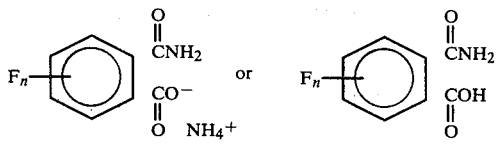

where n is 1 or 2 with an alkali or alkali earth metal hypochlorite to form a fluoroanthranilic acid of the formula

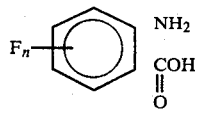

where n is as previously defined; and (B) decarboxylating the fluoroanthranilic acid by reaction with a mineral acid to form a fluoroaniline of the formula

where n is as previously defined.

It will be apparent that the fluoroanthranilic acid produced in step (a) above may be recovered separately. The fluoroanthranilic acids are useful intermediates in the preparation of various other fluorinated aromatic compounds. For example the fluoroanthranilic acid may be reacted in an acidic medium such as hydrochloric acid with sodium nitrite to prepare fluorobenzoic acids.

The ammonium fluorophthalamates utilized in the process of this invention are a novel class of compounds represented by the formula

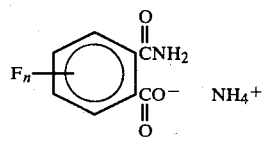

where n is 1 or 2.

The compounds are prepared by the reaction of an chlorophthalic anhydride with potassium or cessium fluoride to form a corresponding fluorophthalic anhydride and subsequent ammonolysis of the fluorophthalic anhydride. Details for the preparation of the ammonium fluorophthalamates are disclosed in co-pending application Ser. No. 220,672, the disclosure of which is hereby incorporated by reference.

The fluorophthalamic acids utilized in the process of this invention are a novel class of compounds represented by the formula

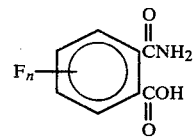

where n is 1 or 2. The compounds are prepared by acidification of ammonium fluorophthalamates. Details regarding the preparation of the fluorophthalamic acids are disclosed in co-pending application Ser. No. 220,674, the disclosure of which is hereby incorporated by reference.

(A) The preparation of fluoroanthranilic acids (step A) by reaction of an ammonium fluorophthalamate or fluorophthalamic with an alkali or alkaline earth metal hypochlorite, preferably sodium hypochlorite, may be carried out over a wide range of temperatures, typically between about 40° and about 100°, and most preferably between about 60° and about 80° Celsius. It is preferred to carry out the reaction at about atmospheric pressure, however, subatmospheric or superatmospheric pressures may be employed, if desired.

The decarboxylation of the fluoroanthranilic acid (step B) is carried out by reaction with an aqueous mineral acid, such as hydrochloric acid, hydrofluoric acid, hydrobromic acid, sulfuric acid, nitric acid, phosphoric acid, and the like. The preferred acid is sulfuric acid. The reaction may be carried out over a wide range of temperatures, such as from about 20° to the reflux temperature of the reaction mixture. Preferably the temperature is maintained in a range of about 75° to about 100° Celsius. The reaction is preferably carried out at atmospheric pressure. Subatmospheric or superatmospheric pressures may be employed but are not generally preferred.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

(A) To a solution of 0.18 parts of sodium hydroxide in 5.0 parts of water was added 0.5 parts of 4,5-difluorophthalamic acid. The solution was heated to about 50° C. and 3.5 parts of 5.7% sodium hypochlorite solution was added. The reaction solution was heated to about 65°-70° and maintained at that temperature range for about 30 minutes then cooled to about 20°-25° C. Concentrated hydrochloric acid was slowly added with the resultant formation of a precipitate. The addition of hydrochloric acid was continued until no further precipitate formed. The mixture was then extracted with chloroform, dried over anhydrous sodium sulfate, filtered, and the remaining chloroform removed under reduced pressure to yield 0.42 parts of 4,5-difluoroanthranilic acid having a melting point of 182°–183° C. The product was analyzed by infra-red spectrographic techniques and liquid phase chromatographic techniques and confirmed to be a high purity (99.0%) 4,5-difluoroanthranilic acid in a yield of 99% based on the starting 4,5-difluorophthalamic acid.

(B) A solution of 0.8 parts of 4,5-difluoroanthranilic acid in 40 parts of 1 N sulfuric acid was placed in a reaction vessel equipped with a reflux condenser. The reaction solution was refluxed for 70 hours, then cooled, basified to a pH of about 8.0–9.0 by addition of 1 N sodium hydroxide, saturated with sodium chloride and extracted with diethyl ether. The mixture was then dried over anhydrous sodium sulfate, filtered, and the diethyl ether removed under reduced pressure to yield 0.54 parts of product. Chromatographic analysis of the product indicated a 78% yield (based on the 4,5-difluoroanthranilic acid) of 96% pure 3,4-difluoroaniline. The structure of the 3,4-difluoroaniline product was confirmed by $C^{13}$ NMR.

EXAMPLE 2

(A) Dimethoxyethane (43 parts) was charged to a reactor and ammonia was bubbled in to form a saturated solution. The ammonia addition was maintained while a solution of 1.84 parts of 4,5-difluorophthalic anhydride in 13 parts of dimethoxyethane was added slowly over a period of 0.5 hours. The reaction mixture was stirred for an additional 5 minute period and the dimethoxyethane was removed by vacuum distillation. The remaining white solid (the ammonium salt of 4,5-difluorophthalamic acid) was dissolved in 20 parts of aqueous sodium hydroxide (40% NaOH) and the solution was de-gassed under moderately reduced pressure to remove any remaining ammonia; then heated at atmospheric pressure, to 50° C. and maintained at tha temperature while 14.1 parts of a 5.78% aqueous sodium hypochlorite solution was added. The solution was then heated to 60°–65° C. and maintained at that temperature, with stirring for about 30 minutes; then cooled to about 20°–25° C. and acidified to a pH of 4–6, by addition of concentrated hydrochloric acid. A precipitate formed and the mixture was extracted with chloroform. The acidification procedure was repeated until no additional precipitate formed. The combined extracts were dried over anhydrous sodium sulfate, filtered, and the chloroform removed by vacuum distillation to yield 1.34 parts of solid 4,5-difluoroanthranilic acid having a melting point of 180°–181° C. The chemical structure of the product was confirmed by infra-red analysis.

(B) Following the procedure of Example 1B, the 4,5-difluoroanthranilic acid was decarboxylated by reaction with sulfuric acid, to form 3,4-difluoroaniline.

EXAMPLE 3

(A) A mixture of 20 parts of 3-chlorophthalic anhydride, and 20 parts of anhydrous potassium fluoride was heated and maintained at about 235° C. for about 9 hours. The reaction mixture was then cooled and the crude product removed by vaccum distillation and recrystallized from chloroform to yield 12.65 parts of purified 3-fluorophthalic anhydride (69% yield).

(B) Ten parts of the 3-fluorophthalic anhydride was dissolved in 78.3 parts of acetonitrile and ammonia was bubbled into the solution until no 3-fluorophthalic anhydride could be detected (by thin layer chromatography on silica gel with a 7:2:1 mixture of toluene:ethyl acetate:acetic acid). The acetonitrile was then removed under reduced pressure to yield 14.8 parts of white solid—a mixture of the ammonium salts of 3- and 6-fluorophthalamic acid.

(C) The mixture of 3- and 6-fluoro ammonium phthalamate salts (14.8 parts) prepared as in 3C, above, was dissolved in 140 parts of a solution of 0.77 M NaOCl and 1.5 M NaOH. The solution was heated and maintained at 80° C. for about 30 minutes, then cooled to about 25° C. and acidified by addition of concentrated hydrochloric acid. An orange precipitate formed, which was extracted with chloroform (3 times) dried over anhydrous sodium sulfate and filtered. The chloroform was removed under reduced pressure leaving 6.9 parts of orange solid having a melting point range of 160°–177° C. The product was analyzed by $C^{13}$ nuclear magnetic resonance techniques and found to be a mixture of 3-fluoroanthranilic acid: 6-fluoroanthranilic acid: three unknowns of 68:20:9:2:1. The 3-fluoroanthranilic acid and 6-fluoroanthranilic acids were separated by recrystallization from chloroform and chromatographic treatment of the mother liquors, using silica gel with chloroform as a solvent. Recrystallization from chloroform, yielded 3.3 parts of 3-fluoroanthranilic acid having a melting point of 181°–182.5° C. and 0.21 parts of 6-fluoroanthranilic acid having a melting point of 168°–169° C.

(D) To a reaction vessel equipped with a reflux condenser and stirring means, was charged 0.155 parts of 3-fluoroanthranilic acid and 10.3 parts of 1 N sulfuric acid. The mixture was heated and maintained at reflux conditions for 75 hours while the process of the reaction was monitored using thin layer chromatography (silica-gel and 7:2:1 solvent mixture of toluene:ethyl acetate:acetic acid). Upon completion the reaction mixture was basified to a pH of about 8.0–9.0 by addition of 1 N sodium hydroxide, saturated with sodium chloride, then extracted with diethyl ether, dried over sodium sulfate and filtered. The remaining diethyl ether was removed under reduced pressure to yield 0.08 parts of o-fluoroaniline. The structure of the final product, o-fluoroaniline, was confirmed by infra-red analysis.

(E) Following the procedure of Example 3D, 6-fluoroanthranilic acid is decarboxylated by reaction with 1 N sulfuric acid to form m-fluoroaniline.

EXAMPLE 4

(A) A solution of 18 parts of sodium hydroxide and 40 parts of ammonium salt of 3-fluorophthalamic acid was heated to 50° C. and 325 parts of aqueous 5.5% sodium hypochlorite solution was added. The solution was heated and maintained at about 65°–70° C. for 30 minutes, then cooled to about 25° C. and acidified by addition of concentrated hydrochloric acid. As the solution was acidified an orange precipitate formed which was extracted with chloroform. The acidification-extraction procedure was repeated until no further precipitate formed during acidification. The chloroform extracts were combined, dried over anhydrous sodium sulfate, filtered, and the chloform removed under reduced pressure, yielding 35 parts of 3-fluoroanthranilic acid.

(B) Following the procedure of Example 3D, the 3-fluoroanthranilic acid is decarboxylated by reaction with 1 N sulfuric acid to yield o-fluoroaniline.

What is claimed is:

1. A process for the preparation of fluoroaniline compounds comprising the steps of
   (A) reacting an ammonium fluorophthalamate or a fluorophthalamic acid of the formula

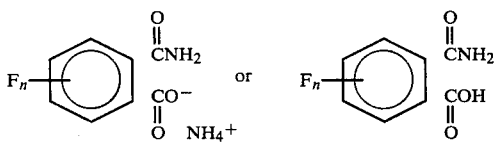

where n is 1 or 2 with an alkali metal or alkali earth metal hypochlorite to form the corresponding fluoroanthranilic acid of the formula

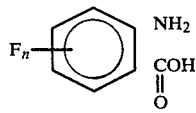

where n is as previously defined, and
   (B) decarboxylating the fluoroanthranilic acid by reaction with a mineral acid to form the corresponding fluoroaniline of the formula

where n is as previously defined.

2. A process according to claim 1 wherein, in the formulas shown, n is 1.

3. A process according to claim 1 wherein, in the formulas shown, n is 2.

4. A process according to claim 1 wherein the oxychloride is an alkali metal hypochlorite.

5. A process according to claim 1 wherein step (A) comprises reacting an ammonium fluorophthalamate of the formula

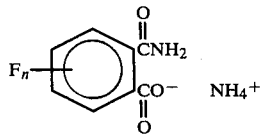

where n is 1 or 2 with a basic reaction medium comprising an alkali or alkali earth metal hydroxide in combination with an alkali or alkali earth metal hypochlorite.

6. A process according to claim 5 wherein the basic reaction medium comprises sodium hydroxide and sodium hypochlorite.

7. A process according to claim 6 wherein 3,4-difluoroaniline is prepared by (A) reacting ammonium 4,5-difluorophthalamate with a basic reaction medium comprising sodium hydroxide and sodium hypochlorite and (B) decarboxylating the resultant 4,5-difluorothranilic acid recovering the resultant 3,4-difluoroaniline.

8. A process according to claim 6 wherein o-fluoroaniline is prepared by
   (A) reacting ammonium 3-fluorophthalamate with a basic reaction medium comprising sodium hydroxide and sodium hypochlorite, and
   (B) decarboxylating the resultant 3-fluoroanthranilic acid and recovering the resultant o-fluoroaniline.

9. A process according to claim 6 wherein m-fluoroaniline is prepared by
   (A) reacting ammonium 6-fluorophthalamate with a basic reaction medium comprising sodium hydroxide and sodium hypochlorite; and
   (B) decarboxylating the resultant 6-fluoroanthranilic acid and recovering the resultant m-fluoroaniline.

10. A process according to claim 1 wherein step (A) comprises reacting a difluorophthalamic acid of the formula

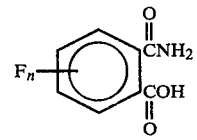

where n is 1 or 2 with a basic reaction medium comprising an alkali or alkali earth metal hydroxide in combination with an alkali or alkali earth metal hypochlorite.

11. A process according to claim 10 wherein the basic reaction medium comprises sodium hydroxide and sodium hypochlorite.

12. A process according to claim 11 wherein 3,4-difluoroaniline is prepared by
    (A) reacting 4,5-difluorophthalamic acid with a basic reaction medium comprising sodium hydroxide and sodium hypochlorite; and
    (B) decarboxylating the resultant 4,5-diflouoroanthranilic acid and recovering the resultant 3,4-difluoroaniline.

13. A process according to claim 11 wherein o-fluoroaniline is prepared by
    (A) reacting 3-fluorophthalamic acid with a basic reaction medium comprising sodium hydroxide and sodium hypochlorite; and
    (B) decarboxylating the resultant 3-fluoroanthranilic acid and recovering the resultant o-fluoroaniline.

14. A process according to claim 11 wherein m-fluoroaniline is prepared by
    (A) reacting 6-fluorophthalamic acid with a basic reaction medium comprising sodium hydroxide and sodium hypochlorite; and
    (B) decarboxylating the resultant 6-fluoroanthranilic acid and recovering the m-fluoroaniline formed.

15. A process for the preparation of difluoroanilines comprising decarboxylating a difluoroanthranilic acid by reaction with an aqueous mineral acid.

16. A process for the preparation of mono-fluoroanilines comprising decarboxylating a monofluoroanthranilic acid by reaction with an aqueous mineral acid.

17. A process according to claim 16 that comprises reacting 3-fluoroanthranilic acid with a mineral acid to form o-fluoroaniline.

18. A process according to claim 16 that comprises reacting 6-fluoroanthranilic acid with a mineral acid to form m-fluoroaniline.

19. A process according to claim 15 that comprises reacting 4,5-difluoroanthranilic acid with a mineral acid to form 3,4-difluoroaniline.

* * * * *